United States Patent [19]

Peck et al.

[11] Patent Number: 4,886,545
[45] Date of Patent: Dec. 12, 1989

[54] COMPOSITIONS COMPRISING 1-SUBSTITUTED AZACYCLOALKANES AND THEIR USES

[75] Inventors: James V. Peck, Costa Mesa; Gevork Minaskanian, Irvine, both of Calif.

[73] Assignee: Nelson Research & Development Company, Irvine, Calif.

[21] Appl. No.: 98,028

[22] PCT Filed: Jan. 29, 1987

[86] PCT No.: PCT/US87/00191
§ 371 Date: Jul. 23, 1987
§ 102(e) Date: Jul. 23, 1987

[87] PCT Pub. No.: WO87/04594
PCT Pub. Date: Aug. 13, 1987

[51] Int. Cl.$^4$ .................. A01N 43/36; A01N 43/40; A01N 43; A01N 46
[52] U.S. Cl. ......................................... 71/88; 71/95; 71/94; 514/946; 514/947; 514/183; 514/212; 514/328; 514/425; 8/564; 8/568; 8/574
[58] Field of Search ............... 71/88, 94, 95; 514/946, 514/947

[56] References Cited

U.S. PATENT DOCUMENTS

| | | | |
|---|---|---|---|
| 4,415,363 | 11/1983 | Radjadhyaksha | 514/946 |
| 4,424,210 | 1/1984 | Radjadhyaksha | 514/946 |
| 4,525,199 | 6/1985 | Radjadhyaksha | 71/88 |
| 4,755,535 | 7/1988 | Minaskainian et al. | 514/946 |
| 4,762,549 | 8/1988 | Radjadhyaksha | 71/88 |

Primary Examiner—Robert T. Bond
Attorney, Agent, or Firm—Walter A. Hackler; Robert J. Baran

[57] ABSTRACT

This invention provides compositions comprising a compound having the structural formula

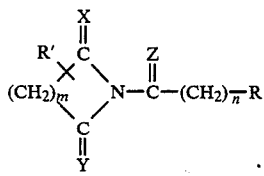

wherein each X, Y and Z may represent oxygen, sulfur or two hydrogen atoms, provided however that, when Z represents two hydrogen atoms, both X and Y represent oxygen or sulfur and when Z represents oxygen or sulfur at least one of X and Y must represent oxygen or sulfur; m is 2–6; R' is H or a lower alkyl group having 1–4 carbon atoms; n is 0–17 and R is —CH$_3$,

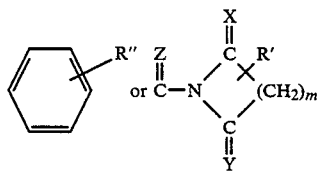

wherein R" is H or halogen. The invention also provides compositions comprising a physiologically-active agent and the hereinabove recited 1-substituted azacycloalkane compound in an amount effective to enhance the penetration of the physiologically-active agent through the skin or other membrane of the body of an animal.

Other compositions of 1-substituted azacycloalkanes and their uses relate to an improved method of dyeing fibers, improved delivery of plant nutrients, improved plant pest control, improved delivery of plant growth regulations, improved acid-catalyzed conversion of a reactant into a reaction product and an improved insect repellant.

6 Claims, No Drawings

COMPOSITIONS COMPRISING 1-SUBSTITUTED AZACYCLOALKANES AND THEIR USES

FIELD OF THE INVENTION

This invention relates to compositions comprising a physiologically-active agent and a 1-alkyl azacycloalkane, which is substituted by oxygen or sulfur atoms pendant from any of the carbon atoms alpha to the nitrogen atom, including the 1-alkyl alpha carbon atom, in an amount effective to enhance the penetration of the physiologically-active agent through the skin or other membrane of the body of an animal.

Other compositions of 1-substituted azacycloalkane and their uses relate to an improved method of dyeing fibers, improved delivery of plant nutrients, improved plant pest control, improved delivery of plant growth regulations, improved acid-catalyzed conversion of a reactant to a reaction product and an improved insect repellant.

BACKGROUND OF THE ART

As hereinabove indicated, the present invention includes a number of uses in which it provides an advantage. Each of these uses will be hereinafter addressed in the order of their recital beginning with the use of the composition of the present invention in the enhancement of the penetration of a physiologically-active agent through the skin or other membranes of body.

It is well known that many physiologically-active agents are best applied topically to obtain desirable results. Topical application, as contrasted to systemic application, can avoid metabolic degradation of the agents, largely avoids side effects of the agents and permits high local concentrations of the agents.

The greatest problem in applying physiologically active agents topically is that the skin is such an effective barrier to penetration. The epidermis of the skin has an exterior layer of dead cells called the stratum corneum which is tightly compacted and oily and which provides an effective barrier against gaseous, solid or liquid chemical agents, whether used alone or in water or oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use to treat such conditions as inflammation, acne, psoriasis, herpes simplex, eczema, infections due to fungus, virus, or other microorganisms, or other disorders or conditions of the skin or mucous membranes, or of conditions beneath the exterior surface of the skin or mucous membranes. The stratum corneum also prevents the skin from absorbing and retaining cosmetic-type materials such as sunscreens, perfumes, mosquito repellants and the like.

Physiologically active agents may be applied to locally affected parts of the body through the vehicle system described herein. Vehicles such as USP cold cream, ethanol and various ointments, oils, solvents, and emulsions have been used heretofore to apply physiologically active ingredients locally. Most such vehicles are not effective to carry significant amounts of physiologically active agents through the skin. One such vehicle is dimethyl sulfoxide.

The 1-lower alkyl substituted azacyclopentan-2-ones having 1–4 carbon atoms in the alkyl group are known to moderately enhance percutaneous absorption of chemicals, e.g., drugs. It was earlier recognized that it would be desirable to obtain the same or higher level of percutaneous absorption with substantially lower concentrations of the penetration-enhancing compound. Therefore, a new class of N-substituted azacycloalkan-2-ones were invented having the desired properties. This new class of penetration-enhancing agents are described in U.S. Pat. Nos. 3,989,815; 3,989,816; 3,991,203; 4,122,170; 4,316,893; 4,405,616; 4,415,563; 4,423,040; 4,424,210; and 4,444,762, which are hereby incorporated by reference.

It is an object of this invention to provide new penetration-enhancing agents having the desirable property of enhancing the percutaneous absorption of physiologically-active agents at concentrations lower than the 1-lower alkyl substituted azacyclopentan-2-ones.

It is also an object of this invention to provide penetration-enhancing agents that are equivalent to the aforesaid new class penetration-enhancing agents described in the above U.S. patents.

Other objects and advantages of the instant invention will be apparent from a careful reading of the specification below.

In this description, the term "animal" includes human beings as well as other forms of animal life, and especially domesticated animals and pets.

SUMMARY OF THE INVENTION

The invention relates to compositions for carrying physiologically active agents through body membranes such as skin and for retaining these agents in body tissues. More specifically, the invention relates to compositions useful in topically administering a physiologically active agent to a human or animal comprising the agent and an effective, non-toxic amount of a compound having the structural formula

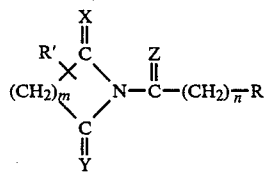

wherein each X, Y and Z may represent oxygen, sulfur or two hydrogen atoms, provided however that, when Z represents two hydrogen atoms, both X and Y represent oxygen or sulfur when Z represents oxygen or sulfur at least one of X and Y must represent oxygen or sulfur; m is 2–6; R' is H or a lower alkyl group having 1–4 carbon atoms; n is 0–16 and R is —CH$_3$,

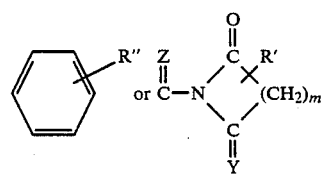

wherein R" is H or halogen.

Preferably R is —CH$_3$ and R' is H.

In a more preferred embodiment of the present invention R is —CH$_3$, R' is H and m equals 4. Even more preferably n is 4–17, e.g. 10.

It has been found that the physiologically active agents are carried through body membranes by the above penetration-enhancing agents and are retained in body tissue.

The invention further relates to the penetration-enhancing agents themselves and their method of making.

It has been found that the hereinabove described 1-substituted azacycloalkanes are also useful in the enhancement of dye penetration in fibers by utilizing in a dyeing process an effective amount of the 1-substituted azacycloalkane. The invention also includes a compound comprising an effective amount of dye and an effective amount of the 1-substituted azacycloalkane.

When combined with a plant nutrient, 1-substituted azacycloalkane provides an improved method of delivery of such plant nutrients by enhancing the uptake and assimilation of the plant nutrients in the plant. The invention also includes a compound comprising an effective amount of a plant nutrient and an effective, delivery-enhancing amount of 1-substituted azacycloalkane.

It has been found that the hereinabove described 1-substituted azacycloalkanes are also useful in an improved method of plant pest control by enhancing the delivery of pesticides to plant pests and the present invention includes a compound comprising an effective amount of a plant pesticide and an effective, delivery-enhancing amount of 1-substituted azacycloalkane.

The compound containing the delivery-enhancing compound and pesticide may be applied directly to the plant pest by topical application or indirectly by topical application to the plants to be protected. The latter indirect method of application enables the pesticide to reach its ultimate site of action, namely, the plant pest, after plant pest has come into contact with the treated plant.

It has been found that the hereinabove described 1-substituted azacycloalkanes are also useful in an improved method of delivery of plant growth regulators and the present invention includes a compound comprising an effective amount of a plant growth regulator and an effective delivery-enhancing amount of 1-substituted azacycloalkane. The plant growth regulators and 1-substituted azacycloalkane compound may be applied to the plant in a conventional manner.

It has been found that the hereinabove described 1-substituted azacycloalkane are also useful as insect repellants, the application and/or delivery of 1-substituted azacycloalkane for such use being by conventional means.

The present invention also provides a process for the conversion of a reactant into a reaction product in the presence of an acid catalyst which comprises contacting said reactant with an acid catalyst comprising a salt of the hereinabove described 1-substituted azacycloalkane.

DETAILED DESCRIPTION OF THE INVENTION

The N-alkyl substituted azacycloalkanes useful as penetration-enhancing additives in the composition of the instant invention may be made by the methods described below. Typical examples of compounds represented by the above structural formula include:
1-n-dodecylazacycloheptan-2,7-dione
1-n-dodecanoylazacycloheptan-2-one
1-n-Octadecanoylazacycloheptan-2-one
1-n-Myristoylazacycloheptan-2-one
1-n-Decanoylazacycloheptan-2-one
1-n-Undecanoylazacycloheptan-2-one
1-n-Tridecanoylazacycloheptan-2-one
1,1'-sebaccylbisazacycloheptan-2-one
1-(4-phenylbutyryl)azacyclohexan-2-one
1-n-hexanoylazacyclooctan-2-one
1,1'-adipoylbisazacycloheptan-2-one
1,1'-adipoyldiazacyclopentan-2-one
1-n-butanoylazacycloheptan-2-one
1-n-heptanoylazacycloheptan-2-one
1-n-pentanoylazacycloheptan-2-one
1-n-hexanoylazacycloheptan-2-one
1-n-octanoylazacycloheptan-2-one
1-n-nonancylazacycloheptan-2-one
1,1'-azelaoylbisazacycloheptan-2-one
1,1'-succinylbisazacycloheptan-2-one
1,1'-suberoylbisazacycloheptan-2-one
1,1'-pimeloylbisazacycloheptan-2-one
1-n-butanoylazacyclooctan-2-one
1-n-pentanoylazacyclohexan-2-one
1-n-butanoneazacyclopentan-2-one
1-n-undecanoylazacyclopentan-2-one
1-n-decanoylazacyclopentan-2-one
1-n-octanoylazacyclopentan-2-one
1-n-octanoylazacyclohexan-2-one
1-n-dodecanoylazacyclopentan-2-one
1-n-dodecylazacyclohexan-2-one
1-n-octadecanoylazacyclohexan-2-one
1-n-hexanoylazacyclohexan-2-one
1-n-butanoylazacyclohexan-2-one
1-n-pentanoylazacyclopentan-2-one
1-n-hexanoylazacyclopentan-2-one Certain of the compounds represented by the above general formula, wherein Z is oxygen, may be prepared by reacting the corresponding azacycloalkan-2-one with an alkanoyl halide in the presence of a base, e.g. sodium hydride. The reaction is carried out under anhydrous conditions in a hydrocarbon solvent, for example, dry toluene at reflux temperature for about 10 to 72 hours in an inert atmosphere, for example, nitrogen. This method is outlined below:

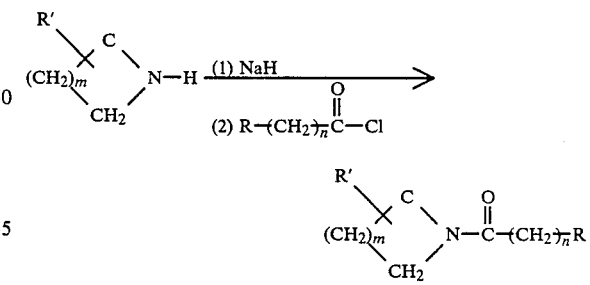

Any of the above compounds, wherein X, Y or Z is oxygen, can be converted to the corresponding sulfur analog by reacting the oxygen-containing compound with phosphorus pentasulfide.

The amount of 1-substituted azacycloalkane which may be used in the present invention is an effective, non-toxic amount for enhancing percutaneous absorption. Generally, this amount ranges between about 0.01 to about 5 preferably about 0.1 to 2 percent by weight of the composition.

The subject compositions may find use with many physiologically active agents which are soluble in the vehicles disclosed.

Fungistatic and fungicidal agents such as, for example, thiabendazole, chloroxine, amphotericin B, candicidin, fungimycin, mystatin, chlordantoin, clotrimazole, miconazole nitrate, pyrrolnitrin, salicylic acid, fezatione, tolnaftate, triacetin and zinc and sodium pyrithione may be dissolved in the penetration-enhancing agents described herein and topically applied to affected areas of the skin. For example, fungistatic or fungicidal agents so applied are carried through the stratum corneum and thereby successfully treat fungus-caused skin problems. These agents, thus applied, not only penetrate more quickly than when applied in the vehicles of the prior art, but additionally enter the animal tissue in high concentrations and are retained for substantially longer time periods whereby a far more successful treatment is effected.

For example, the subject compositions may also be employed in the treatment of fungus infections on the skin caused by candida and dermatophytes which cause athletes foot or ringworm, by dissolving thiabendazole or similar antifungal agents in one of the above-described penetration-enhancing agents and applying it to the affected area.

The subject compositions are also useful in treating skin problems, such as for example, herpes simplex, which may be treated by a solution of iododeoxyuridine dissolved in one of the penetration-enhancing agents or such problems as warts which may be treated with agents such as podophylline dissolved in one of the penetration-enhancing agents. Skin problems such as psoriasis may be treated by topical application of a solution of a conventional topical steroid in one of the penetration-enhancing agents or by treatment with theophylline or antagonists of β-adrenergic blockers such as isoproterenol in one of the penetration-enhancing agents. Scalp conditions such as alopecia areata may be treated more effectively by applying steroids such as triamcinolone acetonide dissolved in one of the penetration-enhancing agents of this invention directly to the scalp.

The subject compositions are also useful for treating mild eczema, for example, by applying a solution of fluocinolone acetonide or its derivatives; hydrocortisone, triamcinolone acetonide, indomethacin, or phenylbutazone dissolved in one of the penetration-enhancing agents to the affected area.

Examples of other physiologically active steroids which may be used with the vehicles include corticosteroids such as, for example, cortisone, cortodoxone, flucetonide, fluorocortisone, difluorsone diacetate, flurandrenolone acetonide, medrysone, amcinafel, amcinafide, betamethasone and its esters, chloroprednisone, clocortelone, descinolone, desonide, dexamethasone, dichlorisone, defluprednate, flucloronide, flumethasone, flunisolide, fluocinonide, flucortolone, fluoromethalone, fluperolone, fluprednisolone, meprednisone, methylmeprednisolone, paramethasone, prednisolone and prednisone.

The subject compositions are also useful in antibacterial chemotherapy, e.g. in the treatment of skin conditions involving pathogenic bacteria. Typical antibacterial agents which may be used in this invention include sulfonamides, penicillins, cephalosporins, penicillinase, erythromycins, lincomycins, vancomycins, tetracyclines, chloramphenicols, streptomycins, etc. Typical examples of the foregoing include erythromycin, erythromycin ethyl carbonate, erythromycin estolate, erythromycin glucepate, erythromycin ethylsuccinate, erythromycin lactobionate, lincomycin, clindamycin, tetracycline, chlortetracycline, demeclocycline, doxycycline, methacycline, oxytetracycline, minocycline, etc.

The subject compositions are also useful in protecting ultra-sensitive skin or even normally sensitive skin from damage or discomfort due to sunburn. Thus, dermatitis actinica may be voided by application of a sunscreen, such as para-aminobenzoic acid or its well-known derivatives dissolved in one of the above-described penetration-enhancing agents, to skin surfaces that are to be exposed to the sun; and the protective paraaminobenzoic acid or its derivatives will be carried into the stratum corneum more successfully and will therefore be retained even when exposed to water or washing for a substantially longer period of time than when applied to the skin in conventional vehicles. This invention is particularly useful in ordinary suntan lotions used in activities involving swimming because the ultraviolet screening ingredients in the carriers of the prior art are washed off the skin when it is immersed in water.

The subject compositions may also find use in treating scar tissue by applying agents which soften collagen, such as aminopropionitrile or penicillamine dissolved in one of the penetration-enhancing agents of this invention topically to the scar tissue.

Agents normally applied as eye drops, ear drops, or nose drops are more effective when dissolved in the penetration-enhancing agents of this invention.

Agents used in diagnosis may be used more effectively when applied dissolved in one of the penetration-enhancing agents of this invention. Patch tests to diagnose allergies may be effected promptly without scratching the skin or covering the area subjected to an allergen when the allergens are applied in one of the penetration-enhancing agents of this invention.

The subject compositions are also useful for topical application of cosmetic or esthetic agents. For example, compounds such as melanin-stimulating hormone (MSH) or dihydroxyacetone and the like are more effectively applied to skin to stimulate a suntan when they are dissolved in one of the penetration-enhancing agents of this invention. The agent is carried into the skin more quickly and in greater quantity when applied in accordance with this invention. Hair dyes also penetrate more completely and effectively when dissolved in one of the penetration-enhancing agents of this invention.

The effectiveness of such topically applied materials as insect repellants or fragrances, such as perfumes and colognes, can be prolonged when such agents are applied dissolved in one of the penetration-enhancing agents of this invention.

It is to be emphasized that the foregoing are simply examples of physiologically active agents including therapeutic and cosmetic agents having known effects for known conditions, which may be used more effectively for their known properties in accordance with this invention.

In addition, the penetration-enhancing agents of the present invention may also be used to produce therapeutic effects which were not previously known. That is, by use of the penetration-enhancing agents described herein, therapeutic effects heretofore not known can be achieved.

As an example of the foregoing, griseofulvin is known as the treatment of choice for fungus infections of the skin and nails. Heretofore, the manner of delivery of griseofulvin has been oral. However, it has long been known that oral treatment is not preferred because of side effects resulting from exposure of the entire body to griseofulvin and the fact that only the outer layers of affected skin need to be treated. Therefore, because fungal infections are generally infections of the skin and nails, it would be advantageous to utilize griseofulvin topically. However, despite a long-felt need for a topical griseofulvin, griseofulvin has been used orally to treat topical fungus conditions because there was not heretofore known any formulation which could be delivered topically which could cause sufficient retention of griseofulvin, in the skin to be useful therapeutically.

However, it has now been discovered that griseofulvin, in a range of therapeutic concentrations between about 0.1% and about 10% may be used effectively topically if combined with one of the penetration-enhancing agents described herein.

As a further example, acne is the name commonly applied to any inflammatory disease of the sebaceous glands; also acne vulgaris. The microorganism typically respponsible for the acne infection is Corynebacterium acnes. Various therapeutic methods for treating acne have been attempted including topical antibacterials, e.g. hexachlorophene, and systemic antibiotics such as tetracycline. While the systemic antibiotic treatments are known to be partially effective, the topical treatments are generally not effective.

It has long been known that systemic treatment of acne is not preferred because of side effects resulting from exposure of the entire body to antibiotics and the fact that only the affected skin need be treated. However, despite a long-felt need for a topical treatment for acne, antibiotics generally have been used only systemically to treat acne because there was not heretofore known an antibacterial formulation which could be used topically which would be effective therapeutically in the treatment of acne. However, it has now been discovered that antibiotics, especially those of the lincomycin and erythromycin families of antibiotics, may be used in the treatment of acne topically if combined with one of the penetration-enhancing agents described herein.

The antibiotics composition so applied is carried into and through the epidermis and deeper layers of the skin as well as into follicles and comedones (sebum-plugged follicles which contain C. acnes) in therapeutically effective amounts and thereby successfully may be used to temporarily eliminate the signs and symptoms of acne.

The term "physiologically active agent" is used herein to refer to a broad class of useful chemical and therapeutic agents including physiologically active steroids, antibiotics, antifungal agents, antibacterial agents, antineoplastic agents, allergens, antihistaminic agents, anti-inflammatory agents, ultraviolet screening agents, diagnostic agents, perfumes, insect repellants, hair dyes, etc.

Dosage forms for topical application may include solution nasal sprays, lotions, ointments, creams, gels, suppositories, sprays, aerosols and the like. Typical inert carriers which make up the foregoing dosage forms include water, acetone, isopropyl alcohol, freons, ethyl alcohol, polyvinylpyrrolidone, propylene glycol, fragrances, gel-producing materials, mineral oil, stearyl alcohol, stearic acid,, spermaceti, sorbitan monooleate, "Polysorbates", "Tweens", sorbital, methyl cellulose, etc.

The amount of the composition, and thus of the physiologically active agent therein, to be administered will obviously be an effective amount for the desired result expected therefrom. This, of course, will be ascertained by the ordinary skill of the practitioner. Due to enhanced activity which is achieved, the dosage of physiologically active agent may often be decreased from that generally applicable. In accordance with the usual prudent formulating practices, a dosage near the lower end of the useful range of the particular physiologically active agent may be employed initially and the dosage increased as indicated from the observed response, as in the routine procedure of the physician.

The invention is further illustrated by the following examples which are illustrative of various aspects of the invention, and are not intended as limiting the scope of the invention as defined by the appended claims.

EXAMPLE 1

Sodium hydride [5.14 g (50% oil dispersion); 0.107 mol] in 100 ml of dry toluene was added to a 500 ml, 3-necked flask fitted with a mechanical stirrer. Azacycloheptan-2-one (10.07 g; 0.089 mol) was dissolved in 50 ml of dry toluene with slight warming and added to the sodium hydride suspension dropwise at room temperature. The suspension was stirred at room temperature for 1 hour. n-Dodecanoyl chloride (19.39 g; 0.089 mol) in 10 ml of dry toluene was added dropwise to the mixture and after the addition was complete, the mixture was stirred overnight at room temperature. The mixture was then washed with water, and the organic layer separated, dried with $MgSO_4$, and concentrated. The resulting yellow oil was distilled 160° C./0.35 mm to yield 1-n-dodecanoylazacycloheptan-2-one as clear oil.

EXAMPLE 2

The compound of Example 1 was tested as a penetration enhancing agent according to the below procedure:

Skin from female hairless mice, 4-6 weeks old, was removed from the animal and placed over penetration wells with normal saline bathing the corium. A plastic cylinder 1.4 cm in diameter was glued onto each piece on the epidermal side. 0.1% triamcinolone acetonide $^3H$ was applied (0.01 cc) to the epidermal surface within the 1.4 cm diameter cylinder. The skin was incubated at room temperature and ambient humidity.

At 6 hours and 24 hours, 2 cc were removed from the 10 cc reservoir of normal saline bathing the corium. The 2 cc of normal saline removed were replaced after the 6 hour sample with 2 cc of normal saline.

The 2 cc aliquots were put into scintillation fluid and the radioactivity determined in a scintillation counter. The amount penetrating was calculated as per cent of dose applied.

In every experiment the $^3H$ triamcinolone acetonide was dissolved in ethanol and the penetration-enhancing agent to be tested was added to the desired concentration.

The controls were ethanol, alone, and 1-n-dodecylazacycloheptan-2-one, a compound described in the U.S. patents, noted above, as having superior penetration-enhancing properties. Five separate tests for the compound of Example 1 and the controls were made and the results averaged.

The results, as reported in the Table below, show that the compound of Example 1 has superior penetration-enhancing properties.

TABLE

| Penetration-Enhancing Agent | Percent Penetration 6 hr. | 24 hr. |
| --- | --- | --- |
| Example 1 | 18.96 | 74.34 |
| 1-n-Dodecylcycloheptan-2-one | 16.64 | 60.94 |
| Ethanol (only) | 0.56 | 6.78 |
| Ethanol (only, repeat) | 0.5 | 5.64 |

As can be shown from the above results the compound of Example 1 shows surprisingly better penetration-enhancing properties than 1-n-dodecylcycloheptan-2-one.

EXAMPLE 3

The following formulation is prepared:

|  | Solution (%) |
| --- | --- |
| Griseofulvin | 1 |
| 1-n-Dodecanoylazacycloheptan-2-one | 1 |
| Isopropyl myristate | 5 |
| Fragrance | 0.1 |
| Ethanol | 92.9 |

This formulation is effective in the treatment of fungus infections.

EXAMPLE 4

An aerosol form of the formulation of Example 3 is prepared by preparing the following mixture:

| Formulation | 25% |
| --- | --- |
| Freon[1] | 75% |

[1]Freon is 75/25 Freon 114/12.

EXAMPLE 5

The following cream formulation is prepared:

|  | % |
| --- | --- |
| Clindamycin base | 1.0 |
| Stearyl alcohol, U.S.P. | 12.0 |
| Ethoxylated cholesterol | 0.4 |
| Synthetic spermaceti | 7.5 |
| Sorbitan monooleate | 1.0 |
| Polysorbate 80, U.S.P. | 3.0 |
| 1-n-Dodecanoylazacycloheptan-2-one | 0.5 |
| Sorbitol solution, U.S.P. | 5.5 |
| Sodium citrate | 0.5 |
| Chemoderm #844 Fragrance | 0.2 |
| Purified water | 68.4 |

This formulation is effective in the treatment of acne.

EXAMPLE 6

The following solution formulations are prepared:

|  | A (%) | B (%) |
| --- | --- | --- |
| Clindamycin base | — | 1.0 |
| Clindamycin phosphate acid | 1.3 | — |
| Sodium hydroxide | 0.077 | — |
| 1.0 M Hydrochloric acid | — | 2.27 |
| Disodium edetate:2H$_2$O | 0.003 | 0.003 |
| Fragrances | 0.5 | 0.5 |
| 1-n-Dodecanoylazacycloheptan-2-one | 1.0 | 1.0 |
| Purified water | 20.0 | 17.73 |
| Isopropanol | 77.12 | 77.497 |

These solutions are effective for the treatment of acne in humans.

EXAMPLE 7

The following solution formulation is prepared:

|  | % |
| --- | --- |
| Neomycin sulfate | 0.5 |
| Lidocaine | 0.5 |
| Hydrocortisone | 0.25 |
| 1-n-Dodecanoylazacycloheptan-2-one | 0.5 |
| Propylene glycol | 98.25 |

This solution is effective for the treatment of otitis in domestic animals.

EXAMPLE 8

The following sunscreen emulsion is prepared:

|  | % |
| --- | --- |
| p-aminobenzoic acid | 2.0 |
| Benzyl alcohol | 0.5 |
| 1-n-Dodecanoylazacycloheptan-2-one | 1.0 |
| Polyethylene glycol 500-MS | 10.0 |
| Isopropyl lanolate | 3.0 |
| Lantrol | 1.0 |
| Acetylated lanolin | 0.5 |
| Isopropyl myristate | 5.0 |
| Light mineral oil | 8.0 |
| Cetyl alcohol | 1.0 |
| Veegum | 1.0 |
| Propylene glycol | 3.0 |
| Purified water | 64.0 |

EXAMPLE 9

The following antineoplastic solution is prepared:

|  | % |
| --- | --- |
| 5-Fluorouracil | 5.0 |
| 1-n-Dodecanoylazacycloheptan-2-one | 0.1 |
| Polyethylene glycol | 5.0 |
| Purified water | 89.9 |

EXAMPLE 10

The following insect repellant atomizing spray is prepared:

|  | % |
| --- | --- |
| Diethyltoluamide | 0.1 |
| 1-n-Dodecanoylazacycloheptan-2-one | 0.1 |
| Ethanol | 99.8 |

EXAMPLE 11

The following lotion formulation may be prepared containing about 0.001 to 1 percent, with preferably 0.1 percent fluocinolone acetonide:

|  | % |
| --- | --- |
| Fluocinolone acetonide | 0.001–1 |
| Cetyl alcohol | 15.0 |
| Propylene glycol | 10.0 |
| Sodium lauryl sulfate | 15.0 |
| 1-n-Dodecanoylazacycloheptan-2-one | 1.0 |
| Water (to make 100%) | |

The steroid is dissolved in the vehicle and added to a stirred, cooling melt of the other ingredients. The preparation is particularly useful for the treatment of inflamed dermatoses by topical application to the affected skin area. The amount and frequency of application is in accordance with standard practice for topical application of this steroid. Penetration of the steroid into the inflamed tissue is enhanced and a therapeutic level is achieved more rapidly and sustained for longer duration than when the steroid is applied in conventional formulations.

EXAMPLE 12

Examples 3–11 are repeated except that 1-n-dodecanoylazacycloheptan-2-one is replaced with the following penetration-enhancing agents:

1-n-dodecylazacycloheptan-2,7-dione   Comparable results are obtained.

Turning now to the use of the composition of the present invention as it relates to the dyeing of fibers, it is well known that additives, or textile auxiliaries are useful in improving or enhancing the dyeing process.

Upon penetration of 1-alkyl azacycloalkanes as hereinabove described, it is useful for enabling the dyeing of fibers at lower temperatures and in shorter times than without the use of 1-alkyl azacycloalkane. Dyeable fibers include both natural and man-made fibers.

Natural fibers suitable for use in the method of the present invention include cotton, linen, wood and silk and others such as kapok, hemp, jute and ramie. Man-made fibers include rayon (fibers composed of regenerated cellulose), acetate (fibers composed of cellulose approximately di- or tri-acetate) and synthetic fibers which are composed of non-natural fiber-forming substances manufactured by chemical methods, such as polyamide, acrylic, polyester and polyolefin.

Typical polyamide fibers include nylons such as, for example, poly(hexamethylene-adipamide), poly (mxylylene adipamide), poly(xylylene sebacamide), polycaprolactom and the like. Typical acrylic fibers are synthetic consisting wholly of polyacrylonitrile or a copolymer of a mixture of acrylonitrile and another vinyl compound, such as Orlon, Dynel, Verel, Creslan, Acrilan, Courtelle and Vinyon. Typical polyester fibers include Terylene, Dacron and Kodel. Typical polyolefin fibers include polyethylene, polypropylene, Vinylon, Rhouyl, Zefran and Darvan.

Various dyestuffs are available and may be classified as substantive or direct dyes, azoic or naphthol dyes, at dyes and sulfur dyes, acid dyes and mordant or metalized dyes, basic or cationic dyes, disperse dyes and fiber reactive dyes.

Direct dyes are soluble in water and are applied primarily to cellulosic fibers and occasionally to protein fibers and polyamides, azoic or naphthol dyes are somewhat similar to developed direct dyes and are used on the same fiber group. Acid dyes and mordant or metalized dyes are used in protein fibers, acrylic fibers, nylon fibers and some modified polyester fibers. Cationic or basic dyes are used especially for coloring acrylic fibers and may be useful with nylon and polyester fibers. Disperse dyes were originally developed for use on acetate fibers and are now used for coloring acetate, polyester, acrylic and polyamide fibers. Reactive dyes are used primarily on cotton, cellulosis, wool, silk and acrylics.

While it is usual to dye most natural fibers in dye liquors at temperatures up to 100° C., these conditions are generally not sufficient to allow the production of deep shades on synthetic fiber materials. Furthermore, while some natural fibers, such as wool, can be satisfactorily dyed in boiling aqueous dye liquors, it usually takes 1½ to 2 hours for the dye to be fully absorbed to produce a deep shade. Wool dyes more slowly than cotton and viscose rayon. For this reason, it is generally not practical to dye wool fabrics by conventional continuous dyeing methods. However, at temperatures above 100° C., wool and synthetic fibers absorb dyes more quickly and thus the continuous dyeing of wool would be possible, except that such high temperature dyeing conditions can result in deterioration of the fiber.

With the use of the compounds described herein, the dyeing process can often be carried out at lower temperatures and completed in a shorter time than without the use of such compounds. Furthermore, use of the compounds described herein enhance the penetration of the dyes into the fiber being dyed and improve fastness. The compounds described herein are especially useful in the dyeing of synthetic fibers for carpet.

The amount of the compounds described herein which may be used in the present invention varies with the desired fiber and dye, the desired time and temperature of dyeing and the dyeing process that is used. Generally, the compounds described herein may be used in amounts of about 0.1 to about 50% by weight and preferably about 1 t about 10% by weight of the dye liquor.

The textile materials with which the compounds of the present invention may be used may be of any type including, but not limited to, a yarn or fabric of any of the known fabric types including woven, knitted or non-woven. An especially suitable fabric is a tufted or looped pile carpet.

As used herein, the term "effective amount" in reference to the textile auxiliary disclosed herein has reference to that amount of the disclosed compound sufficient to improve dye penetration by swelling the fibers to be dyed or dispersing the dye being used in the dyeing process into smaller particles of improving dye fastness, or facilitating the use of lower temperatures and shorter times in the dyeing process.

The l-substituted azacycloalkane is useful in the treatment of plants, in particular to an improved method of the delivery of plant nutrients.

The supply and absorption of chemical compounds needed for growth and metabolism may be defined as nutrition and the chemical compounds required by an organism termed nutrients. The mechanisms by which nutrients are converted to cellular material or used for energetic purposes are metabolic processes. The term 'metabolism' encompasses the various reactions occurring in a living cell in order to maintain life and growth. Nutrition and metabolism are thus very closely interrelated.

The essential nutrients required by green plants are exclusively or inorganic nature. In this respect green plants differ fundamentally from man, animals and a number of microorganisms, which additionally need organic compounds as foodstuffs. An essential element may be defined as one which is required for the normal life cycle of an organism and whose functions cannot be substituted by other chemical compounds. In addition, the element must be shown to be directly involved in nutrition, as for example as a constituent of an essential enzyme system. Based on this definition, the following chemical elements are now known to be essential for higher plants:

| Carbon | C | Potassium | K | Zinc | Zn |
|---|---|---|---|---|---|
| Hydrogen | H | Calcium | Ca | Molybdenum | Mo |
| Oxygen | O | Magnesium | Mg | Boron | B |
| Nitrogen | N | Iron | Fe | Chlorine | Cl |
| Phosphorus | P | Manganese | Mn | Sodium | Na |
| Sulphur | S | Copper | Cu | Silicon | Si |
|  |  |  |  | Cobalt | Co |

The list of essential elements shown above may well not be complete and other elements, in very low concentrations, may yet be shown to be essential for higher plants. For some microorganisms, for example, vanadium (V) has now been established as an essential element.

The plant nutrients may be divided into macronutrients and micronutrients. Macronutrients are found and needed in plants in relatively higher amounts than micronutrients. The plant tissue content of the macronutrient N, for example, is over a thousand times greater than the content of the micronutrient Zn. Following this classification based on the element content in plant material, the following elements may be defined as macronutrients: C, H, O, N, P, S, K, Ca, Mg, Na and Si. The micronutrients are: Fe, Mn, Cu, Zn, Mo, B and Cl. This division of the plant nutrients into macro-and micronutrients is somewhat arbitrary and in many cases differences between the contents of macronutrients and micronutrients are considerably lower than the example cited above.

The process of nutrient uptake and assimilation by plants is not fully understood, although a number of theories of ion uptake and transport are known, see for example, Mengel et al, *Principles of Plant Nutrition,* Chapter 3, "Nutrient Uptake and Assimilation", International Potash Institute, Bern (1978).

The amount of 1-substituted azacycloalkane which may be used in the present invention is an amount effective for enhancing the delivery of a plant nutrient to a plant. Generally, an effective amount ranges between about 0.01 to about 99.9 and preferably about 0.1 to 10 percent by weight of the composition.

Plant nutrients which may be used in this invention include conventional macronutrients and micronutrients previously described including essential as well as non-essential plant nutrients. Examples of nutrients include, but are not limited to, the primary plant foods: nitrogen including ammonia and nitrate ions, phosphorous (phosphoric acid), potassium (potash); the secondary plant-food elements: calcium, magnesium and sulfur; and the trace elements: manganese, boron, copper, zinc, iron molybdenum and chlorine. The form of the foregoing nutrients may be in any conventional form, see, for example, McVickar et al, *Using Commercial Fertilizer,* The Interstate Publishers, Danville, Ill. (1978).

The method of application of the plant nutrient compositions described herein is conventional. See, for example, McVickor et al, *Using Commercial Fertilizers,* Chapter XIV, "Methods of Applying Fertilizers".

The precise amount of the plant nutrient composition to be delivered to the plant will obviously be an effective amount for the desired result expected therefrom. This, of course, will be ascertained by the ordinary skill of the practitioner. Due to enhanced activity which is achieved, the amount of plant nutrients may often be decreased from that generally applicable. In accordance with the usual prudent formulating practices, a dosage near the lower end of the useful range of the particular agent may be employed initially and the dosage increased as indicated from the observed response.

The 1-substituted azacycloalkane as hereinabove described in combination with a pesticide provides a method and composition for plant pest control.

Pesticides are chemicals designed to combat the attacks of various pests on agricultural and horticultural crops. They fall into three major classes: insecticides, fungicides and herbicides (or weed killers). There are also rodenticides (for control of vertebrate pests), nematicides (to kill microscopic eelworms), mollusicides (to kill slugs and snails) and acaricides (to kill mites).

Pesticides may also be divided into two main types, namely contact or nonsystemic pesticides and systemic pesticides. Contact or surface pesticides do not appreciably penetrate plant tissues and are consequently not transported or translocated, within the plant vascular system. The earlier insecticides, fungicides and herbicides were of this type; their disadvantages are that they are susceptible to the effects of weathering (wind, rain and sunlight) over long periods and new plant growth will be left unprotected and hence open to attack by insect and fungal pests. The early agricultural fungicides were, therefore, protectant fungicides—in other words, they are designed to prevent the development of the fungal spores, but once the fungus has become established and infection starts to ramify through the plant tissues such nonsystemic fungicides possess little eradicant action and usually cannot halt the infection.

In contrast, many of the more recent pesticides are systemic in character—these can effectively penetrate the plant cuticle and move through the plant vascular system. Examples are provided by the phenoxyacetic acid selective herbicides, certain organophosphorus insecticides and the more recently discovered systemic fungicides like benomyl.

Systemic fungicides are also sometimes termed plant chemotherapeutants and cannot only protect the plant from fungal attack, but also cure or inhibit an established infection. They are little affected by weathering and will also confer immunity on all new plant growth.

Pests can be divided into various groups. In the plant kingdom, characterized by the ability of the organism to photosynthesize carbohydrates from air and water with the aid of the green pigment chlorophyll, higher plants growing where man does not want them are termed weeds and are important pests. Of the lower plants, algae are not generally of as great importance as pests, although in some circumstances, e.g., in lakes and other slow moving water, excessive algal growth or "bloom" may cause considerable damage and require treatment with chemicals (algicides).

Fungi or nonphotosynthetic plants cannot obtain their nutrients from air and water since they do not have chlorophyll; consequently they feed directly on decaying plant or animal matter (saprophytic fungi) or on living plants or animals (parasitic fungi). There are thousands of different species of fungi mainly found in soil—some, like yeasts, are unicellular while others are composed of a network of branched filaments (hyphae). A number of fungi are serious pests attacking both living crop plants and also crops in storage.

Several bacteria are causal agents of plant diseases, although they are not nearly as important as the phytopathogenic fungi. Bacteria can be observed under the microscope and can be classified according to their shape; thus a spherical bacterium is termed a coccus while a rod-shaped one is a bacillus.

Viruses, like bacteria and fungi, attack plants and animals and some species cause significant plant diseases. Viruses form a distinct category of living organism because they are not true cells. Unlike bacteria they are too small (100–300 A) in diameter to be observed with an ordinary microscope, but they can be revealed under the electron microscope—each virus consists of a single strand of DNA or RNA surrounded by a protective coat of protein.

Several higher animals (vertebrates) are important pests, e.g., mice, rats and rabbits; another group of pests is represented by the true insects (arthropods) which are invertebrates. The latter possess three pairs of legs and the adult body has three parts; the arachnids (mites and ticks) differ from true insects in having no distinct division of the body into three parts; also they usually have four pairs of legs. In the lower orders of animals, certain nematodes, parasitic worms often with unsegmented bodies, are important crop pests.

If pesticides are to be active they must reach the ultimate site of action within the target organism. Thus even surface fungicides, like Bordeaux mixture, must be able to penetrate the fungal spore; similarly contact insecticides have to penetrate the insect cuticle, and contact herbicides the plant cuticle when they impinge on it. The requirements if the pesticides are to be systemic in action are much more stringent because in addition they must have the capacity to be absorbed by the roots or leaves or seeds of plants and be delivered to other parts of the plant. In this way the whole plant, including new growth, is protected from fungal attack, or rendered poisonous to any insect that eats or sucks it.

The amount of 1-substituted azacycloalkane which may be used in the present invention is an amount effective for enhacing the delivery of a pesticide to a plant pest. In the case of indirect application of the active materials to a plant, the enhanced delivery achieved through the use of the 1-substituted axacycloalkane includes improved substantivity and systemic effects of the pesticide. Generally, an effective amount ranges between about 0.01 to about 99.9 and preferably about 0.1 to 10 percent by weight of the pesticide composition.

Suitable pesticides include botanical insecticides such as, for example, nicotine, derris (rotenone) and pyrethrum; synthetic insecticides including dinitrophenols, such as, for example, DNO; organic thiocyanates such as, for example, lethane and thanite, organochlorine insecticides including DDT and related compounds; hexachlorocyclohexane; insecticides containing the cyclodiene group such as, for example, aldrin and dieldren, organophosphorous insecticides including malathion, mevinphos, rogar, dimethtoate, nenozan, miral, diazinon, dursbon, bay-rusil; organocarbonate insecticides including pirimicarb, carbaryl, baygon, propoxur, zectron, carbofuran, aldicarb (Temik), methomul (Lonnate); fungicides including phenylmercury compounds, naban, methan sodium, thiron; compounds containing the n-trichloromethylthio group, such as, for example, captan, folpet and oifolatan; dinitrophenols, including dinocap (Karathane); chlorobenzynes and related compounds, quinones such as, for example, dodine and roural, sulphonamides, benzimidazoles; thiophonates; oxathinns; pyrimadines; piperozine, morpholine and azepine derivatives; organophosphorous compounds including wepsyn, kitazin and conen, herbicides including carboxylic acid herbicides, such as, for example, 2,3-D MCPA, 2,3,6-TBA, IAA, picloram and dichlobenil; chloroaliphatic acids such as dalapan and TCA, and heterocyclic compounds such as atrozine (Gesaprim); triazales such as amitrole, pyrazon, bromacil, endothal; bipyridinum herbicides including paraquat and diquat; benzonitriles; diphenyl ethers; organophosphorour compounds such as, for example, phosphorothiolates such as bensullide; phosphoramidates such as DMPA (Zytron); phosphonates such as glyphosate; plant growth regulators; fumigants; rodenticides including anticoagulants such as warfarin, pidone and norbormide (Raticote); sleep inducing narcotic drugs such as chloralose; gophacide, silatrane and crimidine, nematicides such as dazomet and nellite; molusicides such as metaldehyde, methiocasb and frescon; repellants, antifeeding compounds such as ZIP; chemosterilants, hormones and growth inhibitors. Further examples of pesticides suitable for use in the present invention are known in the art (see, for example, R. Cremlyn, *Pesticides, Preparation and mode of action*, John Wiley and Sons, 1979; F. McEwan et al., *The Use and Significance of Pesticides in the Environment*, John Wiley and Sons, 1979; D. Roberts, *Fundamentals of Plant-Pest Control,* E. H. Freeman and Company, 1978.

The method of application of the pesticide composition described herein is conventional. See, for example, G. Hartley et al., *Chemicals for Pest Control*, Chapter 15, "Application of Pesticides," Pergamon Press, 1969.

The precise amount of the pesticide composition to be delivered to the plant or pest will obviously be an effective amount for the desired result expected therefrom. Most modern pesticides are used in agriculture at a dosage of less than one pound per acre. This, of course, will be ascertained by the ordinary skill of the practitioner. Due to enhanced activity which is achieved, the dosage of agent may often be decreased from that generally applicable. In accordance with the usual prudent formulating practices, a dosage near the lower end of the useful range of the particular agent may be employed initially and the dosage increased as indicated from the observed response.

The 1-substituted azacycloalkanes as hereinabove described in combination with a plant growth regulator is a method and composition for plant growth.

Plant growth regulators are organic compounds, other than nutrients, that, in low concentrations, affect the morphological structure and/or physiological processes of plants. Plant hormones or phytohormones, are naturally occurring growth regulators that in low concentrations control physiological processes in plants. The synthetic growth regulators are used by Man to control such processes as fruit development, fruit thinning, defoliation, growth stimulation and retardation, rooting of cuttings and many other processes. Over the past 30 years the investigation and development of plant growth regulators has been one of the most active areas of fundamental and applied botanical research. The PANS Plant Growth Regulator Index (P. J. Kemp, 25

(2), 211 and 213) under the List of Common and Trade Names and Code Numbers has 492 entries (excluding herbicides except where these are used specifically for some growth regulatory purpose other than weedkilling).

Plant growth regulators that are currently in use at the present time affect a great variety of plant growth processes, including the following (some of the growth regulators in common use are in brackets): rooting of cuttings (indole-butyric acid); promotion of flowering in pineapples (1-napahthalenaecetic acid; B-hydroxyethylhydrazine; ethephon); prevention of preharvest drop of apples (NAA; daminozide); inhibition of turf growth (maleic hydrazide; mefluididediethanolamine); prevention of sprouting of potatoes (maleic hydrazide); floral induction in apple, pear, peach (succinic acid-2,2-dimethylhydrazine; 2,3,5-triiodobenzoic acid); early flowering of 'long day' plants, e.g., lettuce, radish, mustard, dill (gibberellins); flowering of many biennials which normally require low temperatures to flower (gibberellins); improvement of yield of sugar-cane by prevention of flowering (diuron; diquat); delay in flowering in almond and peach to avoid adverse weather conditions (diaminozide); induction of abscission of mature citrus fruits (cyclohexim; 5-chloro-3-methyl-4-nitro-1-H-pyrazole); defoliation of cotton leaves to aid harvesting of bolls (ethephon); thinning of fruit, e.g., grapes, peaches (gibberellic acid; ethephon; 3-chlorophenoxy-α-propionamide); prevention of preharvest drop of citrus (2, 3-dichlorophenoxyacetic acid); induction of fruit set, e.g., in tomato, squash, eggplant, fig (4-chloro-phenoxyacetic acid; 2-naphthyloxyacetic acid); increase in size and quality of grapes (gibberellins); induction of amylase in barley for malting (gibberellins); stimulation of growth of sugar-cane (gibberellins); reduction of stem length in cereals (2-chloroethyl trimethylammonium chloride); development of female flowers, e.g. in pumpkins (NAA; ethephon; daminozide); promotion of male flowers, e.g., in hops (gibberellins); bioregulation of plant composition, e.g., colour in citrus, sugar in sugar-cane, vitamin content in vegetables, increase in dry weight, timing of crop development, increased latex from rubber trees (various growth regulators).

The amount of 1-substituted azacycloalkane which may be used in the present invention is an amount effective for enhancing the delivery of a plant growth regulator to a plant. Generally, an effective amount ranges between about 0.01 to about 99.9 and preferably about 0.1 to 10 percent by weight of the composition.

Suitable plant growth regulators include both natural and synthetic auxins, such as IAA (indolyl-3-acetic acid), IBA (4-[indol-3 yl] butyric acid), NAO (alphanaphthylacetic acid), NOA (2-naththyloxyacetic acid) and NAD (1-naphthylacetamide); phenoxyalkanoic acids, gibberellins, cytokinins, abscisic acid, maleic hydrazide, propham and clorophopham, S,S,S,-tributyl phosphorotrithioate, S,S,S,-Tributyl phosphorotrithioite, chloromequat, daminozide, glyphosine, ancynidol, chlorphonium chloride, dikegulac sodium, morpholinium chloride, fosamine, mefulidide, 4-methoxybenzophenones, PP 528 (ethyl-5-[4-chlorophenyl]-2H-tetrazol-2-yl acetate), piproctanyl bromide, 2-(3-aryl-5-pyrazoyl) benzoic acids, BTS 34723 (1-[N-2-phenoxyethyl)-N-propylcarbamoyl]-1N-imidazole), BTS 34442 (1-[N-2,4-dichlorobenzyl]-N-isopropylcarbamoyl-1N-imidazole), UBI P293 (2,3,-dihydro-5, 6-diphenyl-1,4-oxathiin), M&B 25,105 (propyl 3-t-butyl phenoxyacetate), thidaizuron (N-phenyl-N'-[1,2,3-thiadiazol-5-yl] urea), mepiquat (1,1-dimethylpiperidinium chloride), BAS 09800W (mepiquat chloride plus ethephan), IZAA (5-chloroindazole-8-acetic ethyl ester), MON 8000, DOWCO 242 (tetraisopentyl-ammonium bromide), quarternary ammonium iodides; morphactins including chloroflurecol-methyl, flurecol-butyl, TIBA (2,3,5-triiodobenzoicacid); gametocides including RH 531 (sodium 1-[4-chlorophenyl]-1,2-dihydro-4, 6-dimethyl-2-oxonicotinate), DPX-3778 (3-[4-chlorophenyl]-6-methoxy-1,3,5-triazine-2,4-dione triethanolamine) and allelopathins. Additional plant growth regulators are known in the literature, see, for example, Fletcher et al, Herbicides and Plant Growth Regulators, Chapter 2.

Opportunities for use of plant growth regulators include treatments for seed or seedlings for transplanting which will promote early growth and root development; substances to improve quality (usually protein levels and amino acid balance) of grain crops; substances to improve yield and quality of forages; opportunities in forestry, such as seedling survival and growth, early seed production and accelerated growth rates; systems to reduce energy costs by maximizing response to cultivation, fertilizers (i.e., uptake, mobilization, etc.) and irrigation water; compounds to inhibit ethylene action or production and thus reduce young fruit abscission in indeterminately fruiting crops; new gibberellins with species- or function-specific effects; new applications of known substances based on understanding hormone interactions and storage/inactivation systems ('slow release' compounds) and substances to manipulate natural conjugation reactions; substances to alleviate or minimize effects of plant diseases and insects or to facilitate systems of integrated pest management; substances to modify productivity by reducing photorespiration, dark respiration, or by promoting nitrogen metabolism/fixation, photosynthesis, translocation; substances that intensify synthesis of specific highly desired end-products (oil, protein, cellulose); substances to increase productivity by shifting developmental patterns, such as extending the period of inflorescence differentiation or seed development. The foregoing serves to illustrate the wide range of opportunities available to agricultural chemists.

Plant tissue culture pioneered by White, Steward, Skoog and others, beginning almost as a botanical curiosity, has with the help of growth-regulatory chemicals become a powerful tool in the hands of the plant breeder. It is now possible to tissue culture almost any plant and to develop uniform plantlets from such cultures. even pollen grains can be used and the subsequent haploid plants made polyploid by the use of suitable chemical agents. Together with apical meristem culture there is an unending supply of material.

The method of application of the plant growth regulator composition described herein is conventional. See, for example, W. W. Fletcher and R. C Kirkwood, *Herbicides and Plant Growth Regulators*, Granada Publishing Limited, N.Y., 1982.

The precise amount of the plant growth regulator composition to be delivered to the plant will obviously be an effective amount for the desired result expected therefrom. This, of course, will be ascertained by the ordinary skill of the practitioner. Due to enhanced activity which is achieved, the amount of plant growth regulator may often be decreased from that generally applicable. In accordance with the usual prudent formulating practices, a dosage near the lower end of the useful range of the particular agent may be employed initially and the dosage increased as indicated from the observed response.

This invention provides an improved process for converting reactants, especially organic reactants, to reaction products in the presence of an acid catalyst. The improvement in said process is found in the choice of the compounds which function as the acid catalyst and are defined below. In particular, these compounds increase the rate of reaction, as compared to other well known acid catalysts, e.g., polystyrene sulfonic acids, (which comprises sufonic acid groups pendant from a polystyrene polymer backbone) and are more stable with time and temperature, as compared to said polystyrene sulfonic acid catalysts.

Preferably, the reactants utilized in the process of this invention are hydrocarbons or hydrocarbons substituted with heteroatoms such as nitrogen, oxygen, sulfur, phosphorus and halogen atoms; and especially oxygen atoms.

In another embodiment of this invention, the olefin is contacted with the acid catalyst, described below, in the presence of another reactant to yield reaction products of said olefin and said other reactant. Thus, said second reactant may include a hydroxyl group to yield an ether or an alcohol. For example, alkanols having from one to four carbon atoms may be reacted with olefins having from two to seven carbon atoms in the presence of the acid catalysts described below to yield ethers. Particularly preferred is the reaction of methanol and isobutylene, isoamylene or propylene to yield methyltertiary butyl ether, methyl-tertiary amyl ether or methyl isopropyl ether, respectively. Such reactions may take place at a temperature of from 15° to 200° C. and a pressure of from 1 to 10 atmospheres.

Olefins may also be contacted with a carboxylic acid in the process of this invention to yield esters. Thus, straight chain olefins, having from two to ten carbon atoms, isobutylene or cyclohexene may be reacted in the presence of carboxylic acids having from one to eight carbon atoms at a temperature within the range of 0° C. to 100° C. to yield the corresponding esters as the reaction product. U.S. Pat. No. 3,037,052 to Bortnick gives the details on this general reaction and is hereby incorporated by reference to show specific reactants and reaction conditions. Particularly preferred reactions, within this embodiment of the present process, include the reaction of monoolefins having from one to eight carbon atoms, more preferably from two to four carbon atoms, with methacrylic acid, acrylic acid, acetic acid or phthalic acid to botain the corresponding esters. These esters of acrylic acid and methacrylic acid are useful monomers for the preparation of acrylic plastics and rubbers. The acetate esters, of course are useful as solvents. The phthalic esters are useful as plasticizers.

Other reactants useful in the process of the present invention include alcohols. Thus, in one embodiment of the invention, alcohols having from one to eight carbon atoms, more preferably from one to four carbon atoms, are reacted, in the presence of the acid catalyst described below, to yield either ethers or olefins (by dehydration). For example, methanol or ethanol may be reacted at a temperature of from 40° to 100° C. and a pressure of from 1 to 5 atmospheres to yield dimethyl ether or diethyl ether, respectively. Tertiary butanol may be dehydrated to isobutene at a temperature of from 40° to 100° C. Similarly, butanediol may be dehydrated to tetrahydrofuran.

Like the olefin, alcohols may be reacted in the presence of a second reactant to provide reaction products of said alcohol and said second reactant. In particular, said second reactant may comprise a carboxylic acid group or an aromatic group to yield an ester or an alkylated aromatic, respectively. The reactants and the conditions for these reactions have been described above.

Another reactant that may be used in the process of the present invention is an anhydride. For example, anhydrides, such as acetic anhydride, may be reacted with a compound having an aromatic group or an olefinic group to yield acetylated aromatics or acetylated olefins, respectively. In particular, acetic anhydride may be reacted with anisole to provide p-methoxyacetophenone or with diisobutylene to provide 2,2-methyl, 6-oxo-hept-4-ene. These reactions can be carried out at a temperature of from 40° to 100° C. and a pressure of from 1 to 5 atmospheres.

Aldehydes or ketones may be condensed to provide the respective condensed products by means of the process of the present invention. For example, 2-ethylhexenal may be prepared by condensing two molecules of n-butyraldehyde at a temperature of from 40° to 100° C. and a pressure of from 1 to 5 atmospheres. Similarly, methylisobutyl ketone may be condensed to 1-methyl-4-methyl-6oxo-9-methylnon-4-ene. In general, aldehydes and ketones, having from one to ten carbon atoms, may be condensed to provide dimers thereof in the process of the present invention. In addition, the above aldehydes and ketones may be reacted in the presence of an aromatic compound to obtain the resulting reaction products. In particular, acetone may be reacted with phenol to yield bisphenol A and formaldehyde may be reacted with aniline to yield diaminodiphenylmethane.

Peroxides or hydroperoxides may be decomposed to the corresponding decomposition products by the process of this invention. For example, cumene hydroperoxide may be decomposed to acetone and phenol at low temperatures as compared to the non-acid catalyzed decomposition. Moreover, unlike the prior art polystyrene sulfonic acid catalysts, which are sensitive to heat (and thus the reactor must be designed to remove heat and avoid catalyst degradation), the acid catalysts of this invention are not heat sensitive.

Glycols may be prepared by utilizing an epoxide as the reactant in the process of the present invention. In particular, ethylene oxide and propylene oxide may be converted to ethylene glycol and propylene glycol, respectively.

Esters may be converted, efficiently, to carboxylic acid and alcohol in the present inventive process. Similarly, acetals may be hydrolyzed by this process. For example, sucrose may be hydrolyzed to fructose and glucose.

It is important to note that all of the above examples of reactants, reaction products and reaction conditions are known in the art. The present invention resides in the improvement to such process examples by use salts of the hereinabove described 1-substituted azacycloalkanes, as the acidic catalyst to obtain increased rates of reaction, on an equivalent acid basis, as compared to other known catalysts, such as polystyrene sulfonic acid.

The hereinabove 1-substituted azacycloalkanes are converted into the corresponding quaternary amine salt by reacting with a strong acid, e.g., hydrogen bromide. In particular, such reaction may be carried out as follows:

Gaseous hydrogen bromide is bubbled through a solution of one of the hereinabove 1-substituted azacycloalkanes in diethyl ether to provide an immediate precipitate. Upon saturation of the organic solution with hydrogen bromide, the resultant suspension is filtered and the solid washed with diethyl ether. This is then dried under vacuum to give the hydrogen bromide salt of 1-substituted azacycloalkane.

The above acid catalysts are also useful as acid sources. These salts are stable, non-hydroscopic solids which are useful replacements for solid acid sources known in the prior art. Since they are of known stoichiometric composition, the exact equivalent of any desired amount of acid may be conveniently weighed and safely handled. This offers significant advantage over acid solutions, which are hazardous and must be titrated to determine exact acid content.

As acid sources, examples of the above salts' utility are removal of oxide impurities from a vapor-deposited semi-conductor coating, cleaning metals ranging from solder fluxing agents to household cleaners for plumbing fixtures by the dissolution of inorganic deposit without significantly attacking the base metal, and dissolution of various oxides present in the mill scale formed in the hot rolling process (steel pickling). Thus, these agents function as acid inhibitors. Other processes include converting lignocellulose to hexose and pentose, preparing invert sugar by reaction with a sucrose solution, hydrolyzing starch to obtain sugar syrups, cleaning chemical process equipment including austenitic stainless steel parts in, for example, supercritical steam generators and nuclear power systems, removing from equipment contaminations such as wax from crude oil, tars from coal distillation, oil and grease used for lubrication, special grease-type preservatives used as protective coatings, cleaning and lubricating drilling bits, etc.

The "parent" compounds of the above acid salts are useful as acid scavengers. Thus, for example, excess acid may be removed from acid-washed equipment, acid burns may be treated with these non-toxic agents, trace amounts of acid unacceptable to chemical processes may be precipitated from the reaction solution with these agents, etc.

The invention is further illustrated by the following examples which are illustrative of various aspects of the invention, and are not intended as limiting the scope of the invention as defined by the appended claims.

Example A-1

Dehydration of Alcohols

In this reaction, the reaction rate is monitored by measuring the flow of the olefin, i.e., isobutylene, which is a reaction product arising from the dehydration of tertiary-butanol according to the reaction:

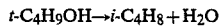

$t\text{-}C_4H_9OH \rightarrow i\text{-}C_4H_8 + H_2O$ in the presence of the acidic catalyst described hereinabove. A small, continuous flow of isobutylene is maintained in the reactor to provide a positive pressure, as well as to initially saturate the t-butanol. (Due to the high solubility of isobutylene in t-butanol, pressurization is required; otherwise, the reaction products, i.e., isobutylene, would dissolve in the reactant, i.e., t-butanol, and would not be observed). The reaction rate is monitored continuously and is the difference between the outlet isobutylene flow and the inlet isobutylene flow.)

To a 500 ml. flask, 100 mg. grams of the catalyst described hereinabove is then added to initiate the dehydration reaction and the resulting two-phase mixture is agitated.

The isobutylene evolved from the t-butanol is measured as a function of time and is taken as an indication of reaction progress; with time=0 taken as the point at which the catalyst is added to the tertiary-butanol. An induction period is observed, after which the reaction rate increases to a maximum and, over a long period of time, the catalyst activity declines as the tertiary butanol becomes rich in reaction product water. The water accumulates at the acid site, thereby "levelling" the acidity.

Example A-2

In this example, the reaction between isobutylene and acetic acid to give tertiary-butyl acetate is catalyzed by the acid catalyst of Example 1. This is accomplished either batchwise or in a continuous flow reactor. At a 2.4 to 3.3 mole ratio of acetic acid to isobutylene, 85 percent conversion to t-butyl acetate, based on isobutylene, is achieved utilizing a fixed bed reactor and 9–10 minutes contact time. Polymerization is not significant as only from a trace to 1.6 percent of $C_8H_{16}$ is detected. The reaction conditions for this reaction is described in U.S. Pat. No. 3,678,099 to Kemp, which is hereby incorporated by reference.

The 1-substituted azacycloalkanes as hereinabove described also are useful as an insect repellant.

Repellants are substances that protect animals, plants, or products, from insect attack by making food or living conditions unattractive or offensive. Compounds, such at the 1-substituted azacycloalkanes of the present invention may be employed to advantage where it is impractical or impossible to use an insecticide and may afford a degree of protection otherwise unattainable for manufactured products, growing plants or the bodies of animals and humans.

The amount of 1-substituted azacycloalkanes which may be used in the present invention is an amount effective for repelling insects and an effective amount in an insect repellant composition generally ranges in an amount between about 0.01 to about 99.9 and preferably about 0.1 to about 10 percent by weight of the composition.

Applications of the 1-substituted azacycloalkanes in accordance with the present invention includes any conventional method of contacting an area, products, animals or humans with the 1-substituted azacycloalkanes of the present invention. Such methods of contacting may include, among others, spraying, soaking (impregnating) dusting and fumigation.

Typical insects which may be effectively repelled are flea beetles, leafhoppers, potato psyllid, Japances beetle, mosquitoes, flied, biting arthropods, mites, ticks, chiggers, termites, poultry mites, carpenter ants, moths, carpet beetles, among others. Of specific importance, the 1-substituted azacycloalkanes may be active as a repellant for anophelis mosquitoes, namatode parasites such as Wuchereria bancrofti and Brugia malayi, the common housefly, blood sucking Triatominae bugs such as the tsetre fly, the biting blackfly, (Simulium damnosun), oriental rat flea, (Xenopsylla Cheopis), ectopic, endotopic parasites in animals, the stable fly, (Stomoxys calcitrans), tick larvae, (Boophilus microplus) and the human louse, (Pediculus Corpois).

While particular embodiments of the invention have been described, it will be understood of course that the invention is not limited thereto since many obvious modifications can be made and it is intended to include within this invention any such modifications as will fall within the scope of the appended claims.

Having now described the invention, we claim:

1. A method for improved delivery of plant nutrients comprising contacting a plant with a composition comprising an effective amount of a plant nutrient and an effective delivery-enhancing amount of compound having the structural formula

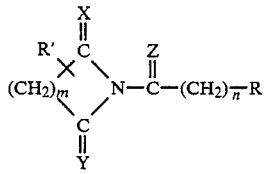

wherein each X, Y and Z may represent oxygen, sulfur or two hydrogen atoms, provided however that, when Z represents two hydrogen atoms, both X and Y represent oxygen or sulfur and when Z represents oxygen or sulfur at least one of X and Y must represent oxygen or sulfur; m is 2-6; R' is H or a lower alkyl group having 1-4 carbon atoms; n is 0-16 and R is —CH$_3$,

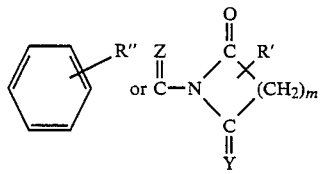

wherein R" is H or halogen

2. A composition comprising an effective amount of a plant nutrient and an effective, delivery-enhancing amount of a compound having the structural formula

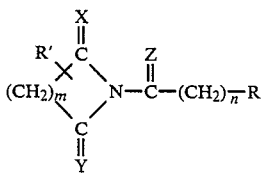

wherein each X, Y and Z may represent oxygen, sulfur or two hydrogen atoms, provided however that, when Z represents two hydrogen atoms, both X and Y represent oxygen or sulfur and when Z represents oxygen or sulfur at least one of X and Y must represent oxygen or sulfur; m is 2-6; R' is H or a lower alkyl group having 1-4 carbon atoms; n is 0-16 and R is —CH$_3$,

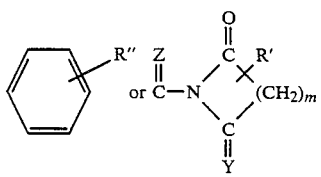

wherein R" is H or halogen.

3. A method for improved pest control comprising contacting a plant or plant pest with a composition comprising an effective amount of a plant pesticide and an effective delivery-enhancing amount of compound having the structural formula

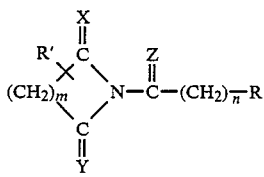

wherein each X, Y and Z may represent oxygen, sulfur or two hydrogen atoms, provided however that, when Z represents two hydrogen atoms, both X and Y represent oxygen or sulfur and when Z represents oxygen or sulfur at least one of X and Y must represent oxygen or sulfur; m is 2-6; R' is H or a lower alkyl group having 1-4 carbon atoms; n is 0-16 and R is —CH$_3$,

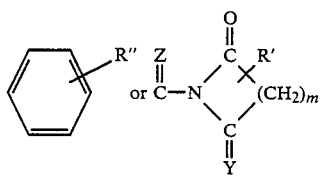

wherein R" is H or halogen.

4. A composition comprising an effective amount of a plant pesticide and an effective, delivery-enhancing amount of a compound having the structural formula

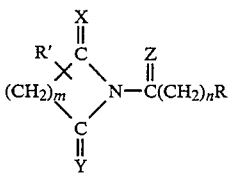

wherein each X, Y and Z may represent oxygen, sulfur or two hydrogen atoms, provided however that, when Z represents two hydrogen atoms, both X and Y represent oxygen or sulfur and when Z represents oxygen or sulfur at least one of X and Y must represent oxygen or sulfur; m is 2-6; R' is H or a lower alkyl group having 1-4 cabon atoms; n is 0-16 and R is —CH$_3$,

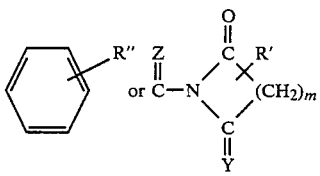

wherein R" is H or halogen.

5. A method for improved delivery of plant growth regulators comprising contacting a plant with a composition comprising an effective amount of a plant growth regulator and an effective delivery-enhancing amount of compound having the structural formula

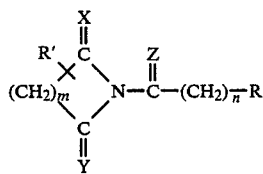

wherein each X, Y and Z may represent oxygen, sulfur or two hydrogen atoms, provided however that, when Z represents two hydrogen atoms, both X and Y represent oxygen or sulfur and when Z represents oxygen or sulfur at least one of X and Y must represent oxygen or sulfur; m is 1–6; R' is H or a lower alkyl group having 1–4 carbon atoms; n is 0–16 and R is —CH$_3$,

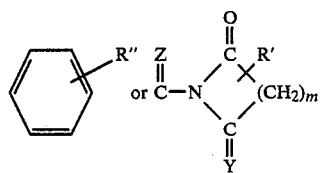

wherein R" is H or halogen.

6. A composition comprising an effective amount of a plant growth regulator and an effective, delivery-enhancing amount of a compound having the structural formula

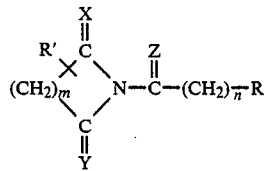

wherein each X, Y and Z may represent oxygen, sulfur or two hydrogen atoms, provided however that, when Z represents two hydrogen atoms, both X and Y represent oxygen or sulfur and when Z represents oxygen or sulfur at least one of X and Y must represent oxygen or sulfur; m is 2–6; R' is H or a lower alkyl group having 1–4 carbon atoms; n is 0–16 and R is —CH$_3$,

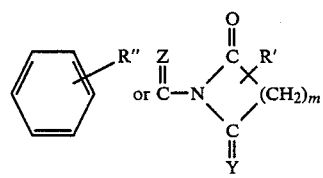

wherein R" is H or halogen.

* * * * *